United States Patent [19]

Andrus et al.

[11] Patent Number: 4,816,571

[45] Date of Patent: Mar. 28, 1989

[54] CHEMICAL CAPPING BY PHOSPHITYLATION DURING OLIGONUCLEOTIDE SYNTHESIS

[75] Inventors: William A. Andrus, San Francisco; J. William Efcavitch, Belmont; Lincoln J. McBride, Redwood City, all of Calif.

[73] Assignee: Applied Biosystems, Inc., Foster City, Calif.

[21] Appl. No.: 58,179

[22] Filed: Jun. 4, 1987

[51] Int. Cl.$^4$ ................... C07H 19/10; C07H 19/20
[52] U.S. Cl. ...................................... 536/27; 536/28
[58] Field of Search ............................. 536/27, 28, 29

[56] References Cited

U.S. PATENT DOCUMENTS 4,458,066 7/1984 Caruthers et al. .................. 536/28

OTHER PUBLICATIONS

Matteucci et al., J. Am. Chem. Soc., 103 (11), 3185-3191 (1981).
Garegg et al., Tetrahedron Letters, 27 (34), 4055-4058 (1986).
Froehler et al., Tetrahedron Letters, 27 (4), 469-472 (1986).
Setlow and Hollaender, "Genetic Engineering Principles and Methods", vol. 4, pp. 1-17.
"Oligonucleotide Synthesis a Practical Approach", Chapter 3 by Atkinson and Smith entitled, Solid-Phase Synthesis of Oligodeoxyribonucleotides by the Phosphitetriester Method, pp. 35-53.
Marvin H. Caruthers, "Gene Synthesis Machines: DNA Chemistry and Its Uses", Oct. 18, 1985, pp. 281-185, Science, vol. 230.
Giles and Morrison, "An Economical System for Automated DNA Synthesis", Mar./Apr. 1987, pp. 16-24.

Primary Examiner—Ronald W. Griffin
Assistant Examiner—Jenny Tou
Attorney, Agent, or Firm—Joseph H. Smith

[57] ABSTRACT

A method is provided for capping failure sequences in oligonucleotide synthesis by phosphitylation. A phosphite monoester is reacted with the 5' or 3' hydroxyl of the failure sequence between successive condensation steps in a synthesis procedure to form a 5' or 3' phosphite diester with the failure sequence. The phosphite diester substituent is inert with respect to subsequent reaction steps in the synthesis of the desired oligonucleotide product.

16 Claims, 1 Drawing Sheet

Lane 1  Lane 2

CHEMICAL CAPPING BY PHOSPHITYLATION DURING OLIGONUCLEOTIDE SYNTHESIS

The invention relates generally to methods for synthesizing oligonucleotides, and more particularly, to the use of phosphite monoesters to chemically cap failure sequences in either DNA or RNA synthesis.

Genes and gene control regions can now be routinely characterized and studied at the molecular level. This has been made possible by recent advances in the technology associated with analyzing, modifying, and synthesizing DNA and RNA. Of particular importance has been the development of machines for the automated synthesis of support-bound single stranded DNA, e.g. Matteucci and Caruthers, *J. Amer. Chem. Soc.*, Vol. 103, pgs. 3185–3191 (1981); and Gait, ed., *Oligonucleotide Synthesis: A Practical Approach* (IRL Press, Washington, D.C., 1984).

The methods of choice for conducting automated DNA synthesis are the phosphoramidite and hydrogen-phosphonate chemistries, e.g. Beaucage and Caruthers, *Tetrahedron Letters*, Vol. 22, pgs. 1859–1862 (1981); McBride and Caruthers, *Tetrahedron Letters*, pgs. 245–248 (1983); Froehler and Matteucci, *Tetrahedron Letters*, Vol. 27, pgs. 469–472 (1986); Garegg et al, *Tetrahedron Letters*, Vol. 27, pgs. 4051–4054 (DNA synthesis) and pgs. 4055–4058 (RNA synthesis)(1986); and Froehler et al, *Nucleic Acids Research*, Vol. 14, pgs. 5399–5407 (1986). A synthetic cycle is repeated under computer control to add one nucleoside monomer unit at a time to achieve the desired sequence and length which defines the oligonucleotide. For example, within the phosphoramidite, or phosphite triester, synthetic cycle several reactions are necessary:

I. Deprotect the reactive functionality (usually a 5' hydroxyl) on the growing chain;

II. Achieve coupling by the addition of a monomer and activator;

III. Cap unreacted 5' hydroxyls to prevent further coupling to failure sequences; and IV. Oxidize the newly formed internucleotide phosphorous linkage to the naturally occurring pentacoordinate state.

The phosphoramidite method is highly optimized, allowing the construction of oligonucleotides as much as 175 nucleotides in length, Efcavitch, S. W., pgs. 65–70 in *Biophosphate and Their Analogues: Synthesis, Structure, Metabolism, and Activity*, Bruzik and Stec, eds. (Elsevier, Amsterdam, 1987). Such performance requires an average yield per cycle of greater than 99%. An essential feature of the synthesis cycle is an effective capping reaction to permanently remove unreacted growing chains from participation in subsequent cycles. Without capping, failure sequences or deletion sequences, those oligonucleotides missing one or more monomeric nucleotides with respect to the desired sequence, will attain a greater average length than they would with capping. The utility of capping is to minimize the length and presence of failure sequences. With capping, a higher concentration of monomeric nucleotide is available to the correctly growing sequences of DNA. Moreover, with an efficient capping reation performed each cycle, the correct sequence DNA, or product, is more easily located, and thus purified by conventional means, such as gel electrophoresis or HPLC. The presence of failure sequences having nearly identical size and composition as the product makes purification extremely difficult.

During phosphoramidite DNA synthesis, failure sequences are capped by acetylation, effected by the concurrent delivery of acetic anhydride and dimethylaminopyridine (DMAP) to the synthesis column. The resulting 5' acetate ester cap prevents the sequence of DNA from participatinag in subsequent condensation reactions in the synthesis. Unfortunately, however, the acetate ester cap is removed during the post-synthesis ammonia cleavage/deprotection step, which makes failure sequence contaminants available to participate in a variety of enzymatic reactions for which the complete sequences were prepared. Such participation, for example, could measurably reduce the efficiency by which DNA linkers are constructed making their use in recombinant vectors more difficult. The availability of a cap which survived the post-synthesis cleavage/deprotection step would be highly useful.

For the hydrogen-phosphonate method, capping by acetylation is not possible. Acetylation capping of the unreacted 5' hydroxyls of failure sequences occurs at a useful rate only by catalysis with a strong base, such as DMAP, N-methylimidazole, or triethylamine. The internucleotide hydrogen phosphonate linkage is modified by phosphorous acetylation under the influence of these strong bases. The phosphorous acetylated residues are then susceptible to cleavage during the post-synthesis cleavage/deprotection step, resulting in internucleotide scission.

It has been claimed that a discrete capping step is unnecessary in the hydrogen-phosphonate method due to acylation of unreacted 5'hydroxyls of failure sequences during the condensation step, e.g. Froehler and Matteucci (cited above) and Froehler et al (cited above). Acylation can occur by esterificaion of 5' hydroxyls by the commonly used acid chloride activators or by the reactive coupling intermediate. The acid chloride activator is present during the coupling reaction to form the reactive coupling intermediate with monomers. However, it has been demonstrated that coupling and acylation can be incomplete during the condensation step, leaving a certain amout of 5' hydroxyl available for increasing the size of failure sequences during subsequent cycles of synthesis. An effective capping operation for hydrogen-phosphonate DNA synthesis is clearly desirable.

SUMMARY OF THE INVENTION

The invention is a method of capping failure sequences in oligonucleotide synthesis by phosphitylation. Preferably, the method involves solid phase, or support-bound, oligonucleotide synthesis by phosphoramidite, phosphotriester, and/or nucleoside hydrogen phosphonate chemistries. Capping is achieved by reacting a phosphite monoester capping agent with the 5' or 3' hydroxyl of the failure sequences between successive condensation steps in the synthesis procedure. The 3' or 5' phosphite diester substituent of the failure sequence is inert with respect to subsequent reaction steps in the synthesis of the desired oligonucleotide product.

As used herein, the term capping refers to reacting either the free 5' hydroxyl of a 3' to 5' growing nucleotide chain or the free 3' hydroxyl of a 5' to 3' growing nucleotide chain with a capping agent to render the chain incapable of participating in subsequent condensation steps. The preferred capping agents of the invention are phosphite monoesters of the form:

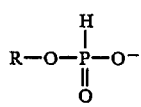

Formula I wherein R, either alone or together with the oxygen to which it is attached, is unreactive with the reagents used in solid phase oligonucleotide synthesis, particularly phosphoramidites or nucleoside hydrogen phosphonates. Preferably, R represents a lower alkyl, an electron-withdrawing substituted lower alkyl, a lower alkyl- or halo-substituted aryl, or a heterocycle containing nitrogen, oxygen, or sulfur and from 5–8 carbon atoms. More particularly, R is methyl, ethyl, propyl, isopropyl, n-butyl, sec-butyl, tert-butyl, n-pentyl, cyclopentylmethyl, isopentyl, neopentyl, n-hexyl, neohexyl, isohexyl, cyclohexylmethyl, betacyclopentylethyl, lower alkyl- or halo-substituted phenyl, lower alkyl- or halo-substituted benzyl, or lower alkyl- or halo-substituted phenylethyl, morpholinyl, thiomorpholinyl, piperidinyl, piperazinyl, beta-electron-withdrawing-substituted ethyl, or the like. In further preference, the electron-withdrawing substituent of beta-electron-withdrawing-substituted ethyl is cyano, nitro, phenylsulphonyl, or phenylester. Most preferably, the beta-electron-withdrawing-substituted ethyl is beta-cyanoethyl. In further preference, the lower alkyl- or halo-substituents of the lower alkyl- or halo-substituted phenyl and benzyl are methyl, chloro, or bromo. In further preference, morpholinyl, thiomorpholinyl, and piperidinyl are morpholino, thiomorpholino, and piperidino, respectively.

As used herein, the term lower alkyl refers to straight-chaind, branched, or cyclic alkyls containing from 1 to 6 carbon atoms.

"Electron-withdrawing" denotes the tendency of a substituent to attract valence electrons of the molecule of which it is apart, i.e. it is electronegative, March, Advanced Organic Chemistry, pgs. 16–18 (John Wiley, New York, 1985).

As used herein, the term oligonucleotide refers to a single stranded chain of either deoxyribonucleotides or ribonucleotides having from a few, e.g. 2–20, to many, e.g. 20 to several hundred or more, nucleotides.

The chemical structures illustrated by Formula I are referred to in the literature as both phosphites and phosphonates. Reflecting the approximate usage in the literature, throughout the structures will be referred to as phosphites, except when R is a nucleoside. In such cases the structure will be referred to as a hydrogen or H-phosphonate.

The present invention overcomes deficiencies in both the nucleoside hydrogen phosphonate and the phosphite triester methods of oligonucleotide synthesis. Use of the capping step in the nucleoside hydrogen phosphonate synthesis process significantly enhances yields by reducing the average length of failure sequences. In both the nucleoside hydrogen phosphonate method and the phosphite triester method, attachment of the capping agents of the invention renders the failure sequences incapable of participating in subsequent biological experiments for which the complete-sequence products are destined, e.g. 5' enzymatic phosphorylation, either for labeling with $^{32}P$, or as a pretreatment for subsequent ligation to other pieces of DNA.

DETAILED DESCRIPTION OF THE INVENTION

Figure 1:
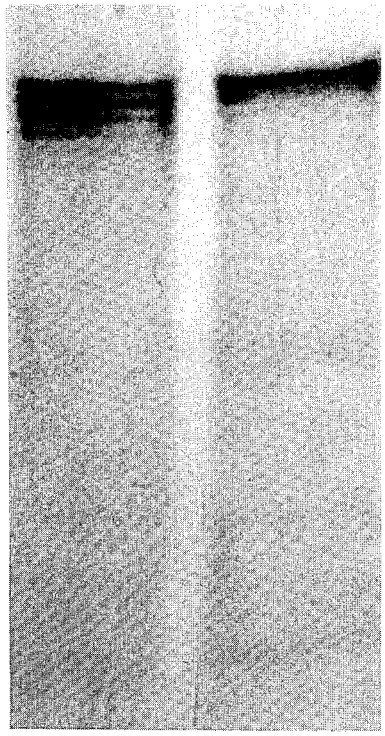
FIG. 1 presents data illustrating the relative purity of reaction products from hydrogen phosphonate syntheses of 34-mer oligonucleotides withou (lane 1) and with (lane 2) the capping step of the invention.

The invention includes a method for capping failure sequences in oligonucleotide synthesis, and methods of synthesizing oligonucleotides which include the capping method of the invention as a step. As illustrated by Formula II, the capping method of the invention comprises reacting a phosphite monoester defined by Formula I, 1, with the free 5' or 3' hydroxyl of a failure sequence, 2, in the presence of a sterically hindered acid chloride, 3, to form a phosphite diester, 4, between the failure sequence and a group which is inert to subsequent reaction steps.

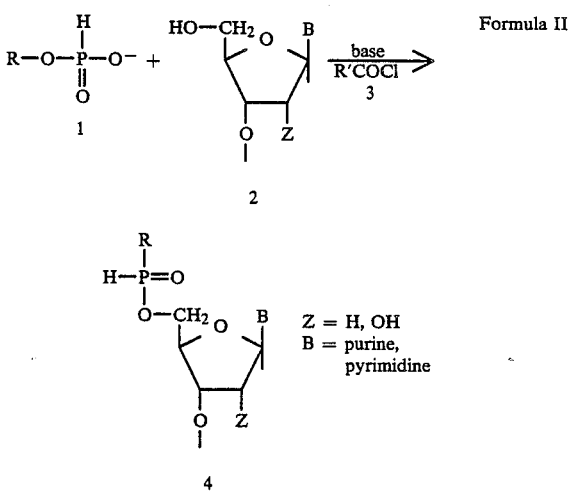

Formula II

Preferably, the capping agents of the invention (1 in Formula III below) are prepared by alkaline hydrolysis of the symmetrical phosphite diesters, 5, as described by Gibbs et al in Synthesis, pgs. 410–413 (1984), which is incorporated by reference. The phosphite monoester 1 can be used directly as a salt after evaporating volatile by products of the reaction or after purification by conventional means.

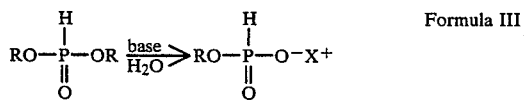

Formula III

In the sterically hindered acid chloride 3, R' is preferably tert-butyl, sec-butyl, cyclohexyl, adamantyl, norbornyl, phenyl, aryl, or the like. More preferably, R' is tert-butyl, norbornyl, or adamantyl. Most preferably, R' is adamantyl.

Preferably, $X^+$ is ammonium, lower alkylammonium, pyridinium, lutidinium, cyclohexylammonium, a metal salt cation such as $Na^+$, $K^+$, $Li^+$, $Ba^+$, $Mg^+$, or the like. More preferably, $X^+$ is triethylammonium, tetrabutylammonium, diisopropylethylammonium, pyridinium, lutidinium, or cyclohexylammonium. Most preferably, $X^+$ is triethylammonium, tetrabutylammonium, or diisopropylammonium.

Preferably, prior to delivery to the synthesis column bearing the oligonucleotide, a phosphite monoester of the invention and its cationic counter ion are dissolved in a solution comprising an aprotic polar solvent, such as acetonitrile, tetrahydrofuran, dichloromethane, or the like, or some combination thereof, and a mild base such as pyridine, picoline, lutadine, collidine, or the like. Pyridine is the most preferred mild base. Preferably, the concentration of the phosphite monoester is between about 0.1 to 1.0 molar. Likewise, the sterically hindered acid chloride (3 in Formula II), prior to delivery to the synthesis column, is dissolved in a solution comprising an aprotic polar solvent, such as acetonitrile, tetrahydrofuran, dichloromethane, or the like, or some combination thereof, and a mild base such as pyridine, picoline, lutadine, collidine, or the like. Pyridine is the most preferred mild base. The respective solutions are delivered concurrently to the synthesis column bearing the growing oligonucleotide so that approximately equimolar amounts of the phosphite monoester and sterically hindered acid chloride are present in the reaction mixture. This operation can be readily performed by an automated DNA synthesizer, such as the Applied Biosystems models 380A, 380B, or 381A. The capping procedure of the invention is performed as a step in each cycle, after the coupling reaction, to render the failure sequences inert. Preferably, the synthesis column is immersed in the reaction mixture for about 20-120 seconds at room temperature, after which the reagents are flushed from the column with a solvent, such as acetonitrile, tetrahydrofuran, dichloromethane, pyridine, or the like, or some combination thereof. All vessels within the instrument must be maintained rigorously free of moisture and oxygen under an atmosphere of an inert gas, such as argon.

Detailed procedures for the phosphite triester and hydrogen phosphonate methods of oligonucleotide synthesis are described in the following references, which are incorporated by reference: Caruthers et al, U.S. Pat. Nos. 4,458,066 and 4,500,707; Matteucci et al, *J. Amer. Chem. Soc.*, Vol. 103, pgs. 3185-3191 (1981); Caruthers et al, *Genetic Engineering*, Vol. 4, pgs. 1-17 (198); Jones, chapter 2, and Atkinson et al, chapter 3, in Gait, ed., *Oligonucleotide Synthesis: A Practical Approach* (IRL Press, Washington, D.C., 1984); Froehler et al, *Tetrahydron Letters*, Vol. 27, Pgs. 469-472 (1986); Garegg et al, *Tetrahedron Letters*, Vol. 27, pgs. 4051-4054 and 4055-4058 (1986); and Froehler et al, *Nucleic Acids Research*, Vol. 14, pgs. 5399-5407 (1986).

The following examples serve to illustrate the present invention. The concentrations of reagents, temperatures, and the values of other variable parameters are only to exemplify the invention and are not to be considered limitations thereof.

EXAMPLES

Example I

Synthesis of Isopropylphosphite Triethylammonium Salt

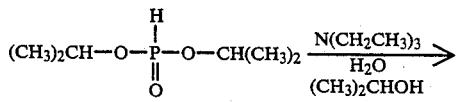

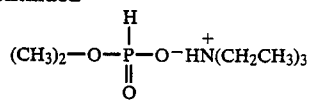

-continued

Diisopropylphosphite (10.0 g, 0.06 moles), triethylamine (14.6 g, 0.14 moles), isopropanol (20 ml), and water (10 ml) were mixed in a flask under an argon atmosphere and heated at 60° C. for 48 hours. The volatile components were removed under vacuum, leaving a viscous, clear oil. The resulting product was produced in 95% yield (12.8 g) and had the following spectral data:

$^1$H nmr (acetone d6, chemical shifts relative to TMS): 10.1+3.3 (d, 1H, J=610 Hz), 4.4 (m 1H), 3.15 (q, 6H, J=7 Hz), 1.35 (d, 6H, J=7 Hz), 1.20 (t, 9H, J=7 Hz)

$^{31}$P nmr (acetone d6, chemical shift relative to $H_3PO_4$): 1.10 ppm J=610 Hz.

Example II

Synthesis of Ethylphosphite Triethylammonium Salt

The triethylammonium salt of ethylphosphite was synthesized by the same procedure as Example I to give a product having the followng spectral data:

$^1$H nmr (acetone d6): 10.0+3.4 (d, 1H, J=599 Hz), 3.85 (q, 2H, J=7 Hz), 3.15 (q, 6H, J=7 Hz), 1.32 (t, 9H, J=9 Hz), 1.20 (t, 3H, J=7 Hz)

$^{31}$P nmr (acetone d6): 0.64 ppm J=599 Hz

Example III

Reaction of Triethylammonium isopropyl phosphite with Thymidine Attached to a Solid Support A solution consisting of 0.1M triethylammonium isopropyl phosphite in 1:1 acetonitrile:pyridine, and a solution consisting of 0.1M 1-adamantane carboxylic acid chloride in 1:1 acetonitrile:pyridine were delivered concurrently to 1.0 micromole of thymidine linked via a 3' succinate to a controlled-pore glass support in an Applied Biosystems model 380B DNA synthesizer. After approximately 30 seconds, the solutions were removed from the column, and the column was washed with acetonitrile. After oxidation of phosphite diester linkage, the product was cleaved from the support with ammonia and subjected to HPLC analysis. By comparison with an authentic sample, it was determined that the major component of the product was 5'-isopropylphosphate thymidine.

Example IV

Synthesis of a 34 Base Oligonucleotide by the Hydrogen Phosphonate Method With and Without Capping The same 34-mer oligonucleotide, 5'-AGGGCCGAGCGCAGAACTGGTCCT-GCAACTTTAT, was twice synthesized by the hydrogen phosphonate method on an Applied Biosystems model 380B DNA synthesizer following the procedure described by Froehler et al (cited above), once including the capping step of the invention, and once excluding the capping step. The capping step was performed using the reagents and reaction conditions of Example III.

FIG. 1 illustrates the results of the gel electrophilic separation of the material cleaved from the respective columns: lane 1 contains the material produced without capping, and lane 2 contains the material produced with capping. The material in both lanes was visualized by UV shadowing. It can be readily seen that the material in lane 2 contains fewer failure sequences near the 34-mer product, as determined by the intensity of lower molecular weight bands near the 34-mer on the gel.

Example V

Synthesis of an 18 Base Oligonucleotide by the Hydrogen Phosphonate Method With and Without Capping The 18-mer oligonucleotide, 5'-TCACAGTCT-GATCTCGAT, was synthesized twice by the hydrogen phosphonate method, once with capping and once without capping, following the same procedure as Example IV. The material cleaved from each column was analyzed by HPLC and the ratio of the correct sequence product to the most prevalent class of failure sequences (17-mers) was determined from the areas under the respective peaks on the chromatograms. The ratio with capping was 33.9. The ratio without capping was 4.9.

The foregoing disclosure of preferred embodiments of the invention has been presented for purpores of illustration and description. It is not intended to be exhaustive or to limit the invention to the precise form disclosed, and obviously many modifications and variations are possible in light of the above teaching. The embodiments were chosen and described in order to best explain the principles of the invention and its practical application, to thereby enable others skilled in the art to best utilize the invention in various embodiments and with various modifications as are suited to the particular use contemplated. It is intended that the scope of the invention be defined by the claims appended hereto.

We claim:

1. A method of capping failure sequences in solid phase oligonucleotide synthesis, the method comprising the step of condensing a capping agent with a hydroxyl of a failure sequence, the capping agent being defined by the formula:

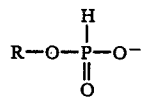

wherein R is straight-chain, branch, or cyclic lower alkyl containing from 1 to 6 carbon atoms, electron withdrawing substituted lower alkyl, lower alkyl-substituted or halo-substituted aryl, or a nitrogen-, oxygen-, or sulfur-containing heterocycle having from 5 to 8 carbon atoms.

2. The method of claim 1 wherein said step of condensing includes reacting said capping agent with said hydroxyl in the presence of a sterically hindered acid chloride.

3. The method of claim 2 wherein R is a straight-chain, branched, or cyclic alkyl containing from 1 to 6 carbon atoms, morpholinyl, thiomorpholinyl, piperidinyl, piperazinyl, or a beta-electron-withdrawing substituted ethyl, and wherein said sterically hindered acid chloride is defined by the formula:

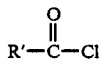

wherein R' is tert-butyl, sec-butyl, cyclohexyl, adamantyl, norbornyl, or phenyl.

4. The method of claim 3 wherein said capping agent is a salt defined by the formula:

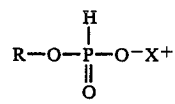

wherein X+ is selected from the group consisting of ammonium, lower alkylammonium, pyridinium, lutidinium, cyclohexylammonium, and metal salt cations.

5. The method of claim 4 wherein X+ is selected from the group consisting of triethylammonium, tetrabutylammonium, diisopropylethylammonium, pyridinium, lutidinium, and cyclohexylammonium.

6. The method of claim 5 wherein X+ is selected from the group consisting of triethylammonium, tetrabutylammonium, and diisopropylammonium.

7. The method of claim 6 wherein R is a straight-chained or branched alkyl of 1 to 4 carbon atoms, phenylethyl, beta-cyanoethyl, morpholino-piperidino, thiomorpholino, or beta-nitroethyl.

8. The method of claim 6 wherein said sterically hindered acid chloride is present in an equimolar amount as said capping agent.

9. A method of synthesizing an oligonucleotide of a predetermined sequence on a solid support, the method comprising the steps of:
(a) deprotecting a 5'-protected oligonucleotide attached to the solid support to form a deprotected oligonucleotide;
(b) reacting a 5'-protected nucleotide monomer with the deprotected oligonucleotide to form either a 5'-protected oligonucleotide or a failure sequence, the failure sequence having a 5' hydroxyl;
(c) capping the failure sequence by reacting a capping agent with the 5' hydroxyl of the failure sequence, the capping agent being defined by the formula:

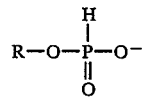

wherein R is lower alkyl, electron-withdrawing substituted lower alkyl, or lower alkyl- or halo-substituted aryl; and
(d) repeating steps (a)–(c) until the oligonucleotide of the predetermined sequence is obtained.

10. The method of claim 8 wherein R of said capping agent is lower alkyl; beta-cyano-, beta-nitro-, beta-phenylsulphonyl-, or beta-phenylester-substituted ethyl; lower alkyl- or halo-substituted phenyl; lower alkyl- or halo-substituted benzyl; morpholino; thiomorpholino; or piperidino; and wherein said step of capping includes reacting said capping agent with said 5' hydroxyl of said failure sequence in the presence of a sterically hindered acid chloride of the formula:

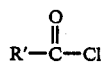

wherein R' is tert-butyl, sec-butyl, cyclohexyl, adamantyl, norbornyl, or phenyl.

11. The method of claim 9 wherein R' is tert-butyl, norbornyl, or adamantyl.

12. The method of claim 10 wherein said capping agent is a salt defined by the formula:

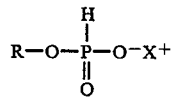

wherein $X^+$ is triethylammonium, tetrabutylammonium, or diisopropylethylammonium.

13. The method of claim 6 wherein R is a straight-chained or branched alkyl of 1 to 4 carbon atoms.

14. The method of claim 6 wherein R is morpholino, piperidino, or thiomorpholino.

15. The method of claim 9 wherein R is a straight-chained or branched alkyl of 1 to 4 carbon atoms.

16. The method of claim 9 wherein R is morpholino, piperidino, or thiomorpholino.

* * * * *